US00PP35921P2

(12) United States Plant Patent
Barendse

(10) Patent No.: US PP35,921 P2
(45) Date of Patent: Jul. 2, 2024

(54) ***RHODODENDRON* PLANT NAMED 'AZAARE02'**

(50) Latin Name: ***Rhododendron* hybrid**
Varietal Denomination: AZAARE02

(71) Applicants: Kwekerij Arends Paterswolde B.V., Paterswolde (NL); Loviflowers BV, Moerbeke-Waas (BE)

(72) Inventor: Matthijs C. Barendse, Paterswolde (NL)

(73) Assignees: KWEKERIJ ARENDS PATERSWOLDE B.V., Paterswolde (NL); LOVIFLOWERS BV, Moerbeke-Waas (BE)

( * ) Notice: Subject to any disclaimer, the term of this patent is extended or adjusted under 35 U.S.C. 154(b) by 0 days.

(21) Appl. No.: 18/101,066

(22) Filed: Jan. 24, 2023

(51) Int. Cl.
*A01H 5/02* (2018.01)
*A01H 6/36* (2018.01)

(52) U.S. Cl.
USPC ..... Plt./239
CPC ..... *A01H 6/364* (2018.05)

(58) Field of Classification Search
USPC ..... Plt./239, 240
CPC ..... A01H 5/02; A01H 5/00
See application file for complete search history.

(56) References Cited

PUBLICATIONS https://www.bloemenkrant.nl/nieuws/algemeen/81908/nominaties-show-your-colours-award-ipm-2023-bekend; Jan. 13, 2023; 2 pages.*
https://www.youtube.com/watch?v=y6dpceNbVBs; Oct. 18, 2018; 1 page.*
https://www-gabot-de.translate.goog/ansicht/starstyle-die-azalee-mit-wow-effekt-411029.html?_x_tr_sl=de&_x_tr_tl=en&_x_tr_hl=en&_x_tr_pto=sc; Jul. 8, 2021; 3 pages.*
Screenshot of a portion of the video https:www.youtube.com/watch?v=y6dpceNBVBs; Oct. 18, 2018; 1 page.*
Pluto UPOVROM Plant Variety Database Citation for 'AZAARE02' as per GB 17/35; May 1, 2022; 1 page.*
https://www-heinje-de.translate.goog/brandheiss/starstyle-azalee-mit-wow-effekt/?_x_tr_sl=de&_x_tr_tl=en&_x_tr_hl=en&_x_tr_pto=sc#1689; Feb. 6, 2021.*
In re Wingen; Feb. 2, 2023; 9 pages.*
https://www-soll--galabau-de.translate.goog/aktuelle-news/ansicht-aktuelles/datum/2021/05/14/stylische-azalee-erobert-gaerten-und-kuebel.html?_x_tr_sl=de&_x_tr_tl=en&_x_tr_hl=en&_x_tr_pto=sc; May 14, 2021; 2 pages.*

* cited by examiner

*Primary Examiner* — Kent L Bell
(74) *Attorney, Agent, or Firm* — Penny J. Aguirre

(57) ABSTRACT

A new cultivar of hybrid *Rhododendron* plant named 'AZAARE02' that is characterized by its uniform and compact plant habit, its floriferous blooming habit, its dense branching habit, its inflorescences with petals that are non-overlapping resulting in a star-shaped appearance, its clearly visible stamens and pollen, its flowers that are bright lilac purple in color, and its leaves that are narrow and long in size.

2 Drawing Sheets

Botanical classification: *Rhododendron* hybrid.
Cultivar designation: 'AZAARE02'.

CROSS REFERENCE TO A RELATED APPLICATIONS

This application is related to a European plant breeders' rights application filed on Oct. 27, 2021, application No. 2021/2567 and to a plant breeders' rights application filed in The United Kingdom on Apr. 30, 2022, Application No. 17/35. The Applicant received the information for the Plant breeders' rights applications directly from the Inventor. This application is also co-pending with a U.S. Plant Patent Applications filed for plants derived from the same breeding program that are entitled *Rhododendron* Plant Named 'AZAARE01' (U.S. Plant patent application Ser. No. 18/101,058) and *Rhododendron* Plant Named 'AZAARE03' (U.S. Plant patent application Ser. No. 18/101,077).

BACKGROUND OF THE INVENTION

The present invention relates to a new and distinct cultivar of *Rhododendron* plant of hybrid origin, botanically known as *Rhododendron* 'AZAARE02' and will be referred to hereafter by its cultivar name, 'AZAARE02'. 'AZAARE02' is a new cultivar of *Rhododendron* shrub grown for use as a landscape plant.

The new invention arose from an ongoing controlled breeding program in Paterswolde, The Netherlands. A goal of the breeding program was to develop hybrid cultivars of *Rhododendron* with flowers that are unique in shape and color.

The Inventor made a controlled cross in 2010 in a test garden in Paterswolde, The Netherlands between two unnamed and unpatented plants from the Inventor's breeding program; the female parent a proprietary seedling of *Rhododendron stenopetalum* X *Rhododendron simsii*) and the male parent designated as 1118-11; a proprietary seedling of *Rhododendron simsii*. 'AZAARE02' was selected in 2016 as a single unique plant amongst the resulting seedlings.

Asexual propagation of the new cultivar was first accomplished by stem cuttings in Paterswolde, The Netherlands in 2016 under the direction the Inventor. Asexual propagation by stem cuttings has determined that the characteristics of the new cultivar are stable and are reproduced true to type in successive generations.

SUMMARY OF THE INVENTION

The following traits have been repeatedly observed and represent the characteristics of 'AZAARE02'. These attributes in combination distinguish 'AZAARE02' as a new and distinct cultivar of *Rhododendron*.

1. 'AZAARE02' exhibits a uniform and compact plant habit.
2. 'AZAARE02' exhibits a floriferous blooming habit.
3. 'AZAARE02' exhibits a dense branching habit.
4. 'AZAARE02' exhibits inflorescences with petals that are non-overlapping resulting in a star-shaped appearance.
5. 'AZAARE02' exhibits clearly visible stamens and pollen.
6. 'AZAARE02' exhibits flowers that are bright lilac purple in color.
7. 'AZAARE02' exhibits leaves that are narrow and long in size.

Both parent plants of 'AZAARE02' differ from 'AZAARE02' in having less compact and more open and less uniform plant habits and inflorescences that lack the star-shaped appearance of 'AZAARE02'. 'AZAARE02' can also be most closely compared to the *Rhododendron* cultivars 'Kinku Saku' (U.S. Plant Pat. No. 17,177), 'AZAARE01' and 'AZAARE03'. 'Kinku Saku' differs from 'AZAARE02' in having flowers that are pink in color, flower petals that are touching, and a shorter and later blooming period. 'AZAARE01' is similar to 'AZAARE02' in being similar in size and in having flowers with petals that are non-overlapping. 'AZAARE01' differs from 'AZAARE02' in having flowers that are bright pink in color. 'AZAARE03' differs from 'AZAARE02' in having flowers that are white-purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales that fall within a one-year grace period prior to the filing date. Disclosures include website listings by Thompson-Morgan, Suttons, Provender Nurseries, Green Leaf, and Cowell's Garden Centre.

BRIEF DESCRIPTION OF THE DRAWINGS

The accompanying color photographs illustrate the overall appearance and distinct characteristics of the new *Rhododendron*. The plant in the photograph is 20-months in age as grown outdoors with 3 plugs in a 19-cm container in Moerbeke, Belgium.

The photograph in FIG. 1 provides a side view of 'AZAARE02' in bloom.

Figure 1:
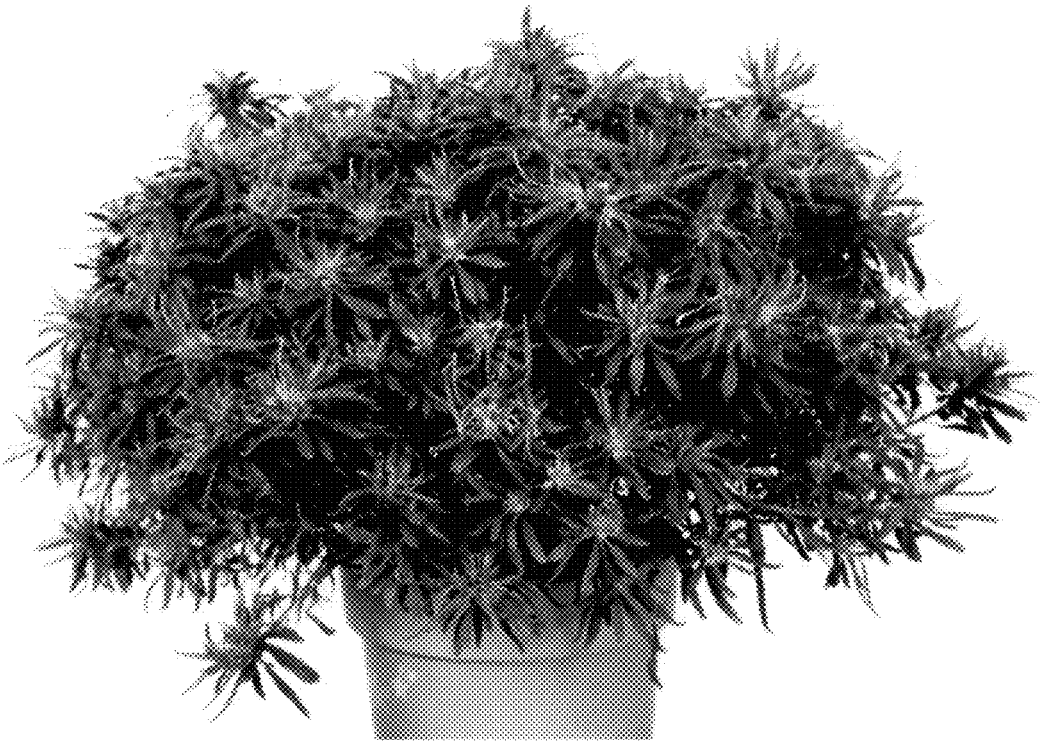
Figure 2:
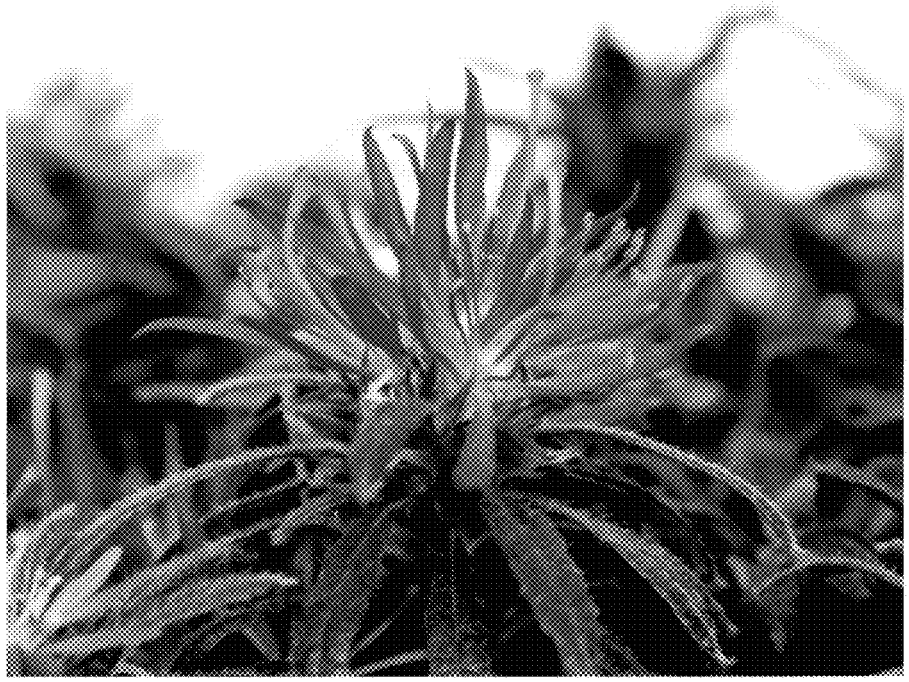

The photograph in FIG. 2 provides a close-up view of the inflorescences of 'AZAARE02'.

Figure 3:
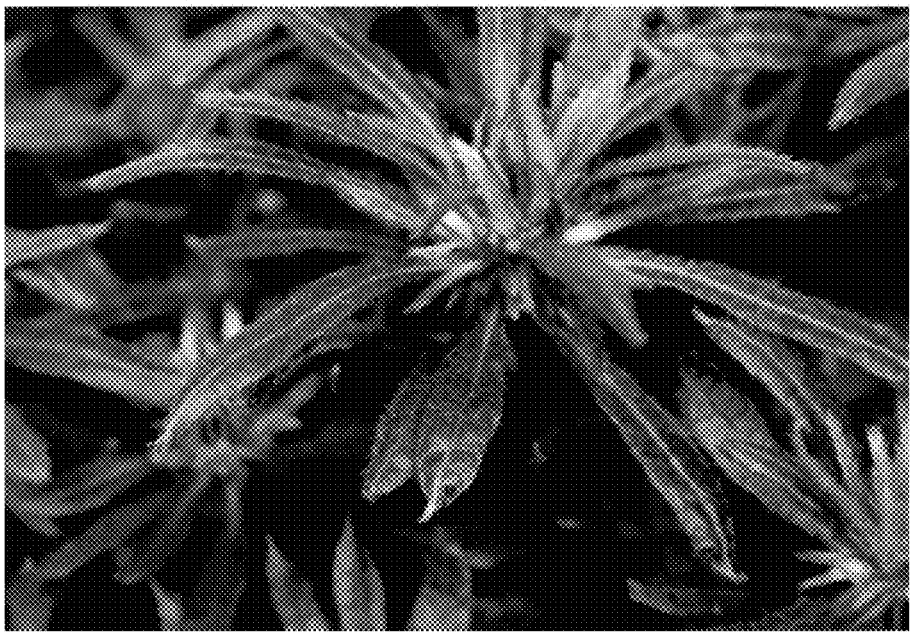

The photograph in FIG. 3 provides a close-up view of the foliage of 'AZAARE02'.

The colors in the photographs are as close as possible with the digital photography and printing techniques utilized and the color codes in the detailed botanical description accurately describe the new *Rhododendron*.

DETAILED BOTANICAL DESCRIPTION OF THE PLANT

The following is a detailed description of 20-month-old plants of the new cultivar as grown outdoors with 3 plugs in a 19-cm container in Moerbeke, Belgium. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General characteristics:

*Blooming period.*—April to May in The Netherlands.
*Plant type.*—Evergreen shrub.
*Plant habit.*—Dense, uniform growth, and compact plant habit.
*Height and spread.*—29.2 cm in height (soil level to top of foliar plane), 29.8 cm in height (soil level to top of floral plane), 33.4 cm in spread as grown with 3 plugs in a 19-cm container, reaches 50 cm in height and spread in the landscape.
*Hardiness.*—At least in U.S.D.A. Zones 8 to 12.
*Diseases and pests.*—No susceptibility or resistance to pests or diseases has been observed.
*Root description.*—Fibrous.
*Propagation.*—Stem cuttings.
*Growth rate.*—Moderate to high.
*Root development.*—4 weeks for root initiation and 1.5 years to produce a marketable plant from a rooted cutting.

Stem description:

*Shape.*—Round.
*Stem color.*—Young; 151A, mature; 165A, older stems and bark; 165A, N199B and N199C.
*Stem size.*—Average of 11 cm in length, 2 mm in diameter.
*Stem surface.*—Very slightly glossy.
*Stem aspect.*—Average of 40° (varying between 30° and 50°).
*Stem strength.*—Strong.
*Branching.*—Densely branched, 6 main branches, 40 lateral branches.
*Internode length.*—4 mm.

Foliage description:

*Leaf shape.*—Narrow oblong to narrow oblanceolate.
*Leaf division.*—Simple.
*Leaf base.*—Attenuate.
*Leaf apex.*—Acute, often with a mucronate tip.
*Leaf venation.*—Anastomosing, upper surface; 148A in color, lower surface; 148B in color.
*Leaf margins.*—Finely repand, moderately revolute and finely undulate.
*Leaf attachment.*—Petiolate.
*Leaf arrangement.*—Alternate, leaf clusters whorled at terminal shoot apex.

*Leaf orientation*.—Horizontal, sometimes curved slightly upward.

*Leaf aspect*.—Flat to very slightly wavy (lamina).

*Leaf surface*.—Both surfaces glossy and moderately rugose, moderately covered with very short hairs, 0.2 mm in length, 172B in color, margin hairs N170B to N170C.

*Leaf color*.—Young leaves upper surface; 137C to 137D, young leaves lower surface; 138B in color, mature and fall leaves upper surface; a blend of 147A and N189A, mature and fall leaves lower surface; a blend of 138B and 147B.

*Leaf size*.—Average of 3.1 cm in length, 5 mm in width.

*Petioles*.—Average of 7 mm in length and 1.25 mm in diameter, strong, upper surface color 145A, lower surface color 151C, both surfaces slightly glossy and moderately covered with short hairs; 2 mm in length and N170B in color.

Flower description:

*Inflorescence type*.—Terminal clusters.

*Lastingness of flowers*.—Average of 10 days.

*Inflorescence size*.—Average of 4.2 cm in height and 6.3 cm in diameter.

*Flower quantity*.—Average of 4 per inflorescence, 60 per plant.

*Flower size*.—An average of 5.5 cm in diameter and 3 cm in height.

*Flower fragrance*.—None.

*Flower type*.—Rotate, single.

*Flower aspect*.—Upright to outward.

*Flower bud*.—Obovate in shape, 8 mm in length, 1 cm in diameter, surface is smooth slightly glossy, and glabrous, color; 65A, base 144C and 145A.

*Tepals*.—5, non-overlapping, whorled in 1 row, unfused, 3.0 cm in length, 6 mm in width, lanceolate to narrow lanceolate in shape, slightly carinate, apex narrow acute, base cuneate, margins entire, upper surfaces smooth, glabrous, lower surface pubescent, upper surface slightly glossy, lower surface matte, moderately to densely covered with very short strigose hairs, average length: 1.0 mm, colored N155A and 177A, when opening upper surface; N74A, when opening lower surface; 71B, fully open upper surface; 71C, fully open lower surface; 71B to 71C.

*Calyx*.—Rotate, 9 mm in length, 1.5 cm in diameter.

*Pedicels*.—8 mm in length, 1.5 mm in diameter, average of 25° angle to lateral branch (varying between vertical and 50°), moderately strong, 145A in color, surface is very slightly glossy and moderately covered with soft hairs, an average of 1 mm in length, NN155D in color.

Reproductive organs:

*Gynoecium*.—Pistil; 1, stigmas; club-shaped, 173C in color, 1.5 mm in length, 2 mm in diameter, style; average 3.25 cm in length, color; 63A, ovary; 143A in color, densely covered with soft hairs, 1.5 mm in length, NN155D in color.

*Androecium*.—Stamens; 10, filaments; 2.6 cm in length, 71C to 71D in color, anthers; dorsifixed, obovate in shape, 2 mm in length, 1 mm in width, 197B in color; pollen; 156D in color, low in quantity.

*Fruit/seeds*.—No fruit or seed observed.

It is claimed:

1. A new and distinct cultivar of *Rhododendron* plant named 'AZAARE02' as herein illustrated and described.

* * * * *